US010448951B2

(12) United States Patent
Stevenson et al.

(10) Patent No.: US 10,448,951 B2
(45) Date of Patent: Oct. 22, 2019

(54) ABDOMINAL WALL TREATMENT DEVICES

(75) Inventors: Eric Stevenson, San Antonio, TX (US);
Wendell Sun, Warrington, PA (US);
Aaron Barere, Hoboken, NJ (US)

(73) Assignee: LifeCell Corporation, Madison, NJ (US)

( * ) Notice: Subject to any disclaimer, the term of this patent is extended or adjusted under 35 U.S.C. 154(b) by 406 days.

(21) Appl. No.: 13/029,487

(22) Filed: Feb. 17, 2011

(65) Prior Publication Data

US 2011/0208320 A1 Aug. 25, 2011

Related U.S. Application Data

(60) Provisional application No. 61/306,006, filed on Feb. 19, 2010.

(51) Int. Cl.
*A61B 17/08* (2006.01)
*A61B 17/00* (2006.01)
*A61F 13/00* (2006.01)

(52) U.S. Cl.
CPC ............ *A61B 17/08* (2013.01); *A61B 17/085* (2013.01); *A61B 2017/00004* (2013.01); *A61F 2013/00451* (2013.01)

(58) Field of Classification Search
CPC ... A61B 17/08; A61B 17/095; A61B 17/0057; A61B 2017/00004; A61F 2013/00451; A61F 2002/0068; A61F 2002/0072; A61F 13/14; A61F 13/148
USPC .............. 606/151, 213, 215, 216; 623/23.72, 623/23.73–23.76
See application file for complete search history.

(56) References Cited

U.S. PATENT DOCUMENTS

| | | |
|---|---|---|
| 4,034,750 A | 7/1977 | Seiderman |
| 4,796,603 A | 1/1989 | Dahlke et al. |
| 4,841,962 A | 6/1989 | Berg et al. |
| 4,854,316 A | 8/1989 | Davis |
| 5,336,616 A | 8/1994 | Livesey et al. |
| 5,364,756 A | 11/1994 | Livesey et al. |
| 5,425,740 A * | 6/1995 | Hutchinson, Jr. .... A61B 17/122 227/902 |
| 5,634,931 A | 6/1997 | Kugel |
| 5,780,295 A | 7/1998 | Livesey et al. |
| 5,972,007 A | 10/1999 | Sheffield et al. |
| 6,113,623 A | 9/2000 | Sgro |
| 6,174,320 B1 | 1/2001 | Robert et al. |

(Continued)

FOREIGN PATENT DOCUMENTS

| | | |
|---|---|---|
| DE | 2 303 444 | 5/1974 |
| DE | 10 2009 020 763 | 11/2009 |

(Continued)

OTHER PUBLICATIONS

Burns et al., "Non-Cross-Linked Porcine Acellular Dermal Matrices for Abdominal Wall Reconstruction", Plastic and Reconstructive Surgery Journal, 125(1), pp. 167-176, Jan. 2010.*

(Continued)

*Primary Examiner* — Shaun L David
(74) *Attorney, Agent, or Firm* — McCarter & English, LLP (57) ABSTRACT

Devices and methods for treating or repairing openings in an body wall are provided. The devices and methods can include acellular tissue matrices. The tissue matrices can be positioned within the abdominal opening and can be used to close the opening.

20 Claims, 7 Drawing Sheets

(56) References Cited

U.S. PATENT DOCUMENTS

| | | | |
|---|---|---|---|
| 6,179,872 B1 | 1/2001 | Bell et al. | |
| 6,194,136 B1 | 2/2001 | Livesey et al. | |
| 6,197,036 B1 | 3/2001 | Tripp et al. | |
| 6,381,026 B1 | 4/2002 | Schiff et al. | |
| 6,599,318 B1 | 7/2003 | Gabbay | |
| 6,610,006 B1 | 8/2003 | Amid et al. | |
| 6,638,284 B1 | 10/2003 | Rousseau et al. | |
| 6,652,559 B1 | 11/2003 | Tetreault et al. | |
| 6,726,660 B2 | 4/2004 | Hessel et al. | |
| 6,790,213 B2 | 9/2004 | Dennis et al. | |
| 6,833,408 B2 | 12/2004 | Sehl et al. | |
| 6,843,767 B2 * | 1/2005 | Corcoran et al. | 600/37 |
| 6,933,326 B1 | 8/2005 | Griffey et al. | |
| 7,105,001 B2 | 9/2006 | Mandelbaum | |
| 7,163,563 B2 * | 1/2007 | Schwartz et al. | 623/23.76 |
| 7,235,295 B2 | 6/2007 | Laurencin et al. | |
| 7,358,284 B2 | 4/2008 | Griffey et al. | |
| 2002/0099344 A1 | 7/2002 | Hessel et al. | |
| 2002/0103542 A1 | 8/2002 | Bilbo | |
| 2003/0035843 A1 | 2/2003 | Livesey et al. | |
| 2003/0119985 A1 | 6/2003 | Sehl et al. | |
| 2003/0143207 A1 | 7/2003 | Livesey et al. | |
| 2003/0225355 A1 | 12/2003 | Butler | |
| 2004/0078077 A1 | 4/2004 | Binette et al. | |
| 2004/0078089 A1 | 4/2004 | Ellis et al. | |
| 2004/0220591 A1 | 11/2004 | Bonutti | |
| 2005/0009178 A1 | 1/2005 | Yost et al. | |
| 2005/0015088 A1 * | 1/2005 | Ringeisen | 606/69 |
| 2005/0028228 A1 | 2/2005 | McQuillan et al. | |
| 2005/0043716 A1 | 2/2005 | Frimer | |
| 2005/0049638 A1 | 3/2005 | Mandelbaum | |
| 2005/0054771 A1 | 3/2005 | Sehl et al. | |
| 2005/0058629 A1 | 3/2005 | Harmon et al. | |
| 2005/0085757 A1 | 4/2005 | Santanello | |
| 2005/0288691 A1 | 12/2005 | Leiboff | |
| 2006/0073592 A1 | 4/2006 | Wendell et al. | |
| 2006/0105026 A1 | 5/2006 | Fortune et al. | |
| 2006/0106419 A1 | 5/2006 | Gingras | |
| 2006/0235511 A1 | 10/2006 | Osborne | |
| 2006/0247206 A1 | 11/2006 | Feins | |
| 2006/0276908 A1 | 12/2006 | Sogaard-Andersen et al. | |
| 2007/0111937 A1 | 5/2007 | Pickar et al. | |
| 2007/0202173 A1 | 8/2007 | Cueto-Garcia | |
| 2007/0248575 A1 | 10/2007 | Connor et al. | |
| 2007/0293878 A1 | 12/2007 | Butsch | |
| 2008/0027542 A1 | 1/2008 | McQuillan et al. | |
| 2008/0033461 A1 | 2/2008 | Ferdinand et al. | |
| 2008/0071300 A1 | 3/2008 | Popadiuk et al. | |
| 2008/0091277 A1 | 4/2008 | Deusch et al. | |
| 2008/0095819 A1 | 4/2008 | Gourdie et al. | |
| 2008/0113035 A1 | 5/2008 | Hunter | |
| 2008/0131509 A1 | 6/2008 | Hossainy et al. | |
| 2008/0147199 A1 | 6/2008 | Yost et al. | |
| 2008/0167729 A1 | 7/2008 | Nelson et al. | |
| 2009/0035289 A1 | 2/2009 | Wagner et al. | |
| 2009/0306790 A1 | 12/2009 | Wendell | |
| 2011/0004306 A1 * | 1/2011 | Harper | 623/14.13 |
| 2011/0015760 A1 * | 1/2011 | Kullas | 623/23.72 |
| 2011/0295283 A1 * | 12/2011 | Darois et al. | 606/151 |

FOREIGN PATENT DOCUMENTS

| | | |
|---|---|---|
| JP | 2002-186581 A | 7/2002 |
| WO | WO 2000/16822 | 3/2000 |
| WO | WO 2008/060973 | 5/2008 |
| WO | WO 2009075786 A1 * | 6/2009 |

OTHER PUBLICATIONS

Candage et al., "Use of Human Acellular Dermal Matrix for Hernia Repair: Friend or Foe?" Journal of Surgery, 144(4), pp. 703-711, Oct. 2008.*

Gupta et al., "Ventral Herniorrhaphy: Experience with Two Different Biosynthetic Mesh Materials, Surgisis and Alloderm", Hernia, 2006(10), pp. 419-425, Aug. 2006.*

Buinewicz et al., "Acellular Cadaveric Dermis (AlloDerm): A New Alternative for Abdominal Hernia Repair", Annals of Plastic Surgery, 52(2), pp. 188-194, Feb. 2004.*

Eberli, Daniel et al. "In vivo evalulation of acellular human dermis for abdominal wall repair" Journal of Biomedical Materials Research Part A. vol. 93 (4) pp. 1527-1538 Published online Dec. 14, 2009.*

Aycock et al., "Parastomal Hernia Repair With Acellular Dermal Matrix," *J. Wound Ostomy Continence Nurs.* (2007), p. 521-523, 34(5).

Greenstein et al., "Parastomal Hernia Repair Using Cross-Linked Porcine Dermis: Report of a Case," *Surg. Today* (2008), p. 1048-1051, 38.

Hammond et al., "Human in vivo Cellular Response to a Cross-Linked Acellular Collagen Implant," *British Journal of Surgery* (2008), p. 438-446, 95.

Hammond et al., "Parastomal Hernia Prevention Using a Novel Collagen Implant: A Randomised Controlled Phase 1 Study," *Hernia* (2008), p. 475-481, 12.

Inan et al., "Laparoscopic Repair of Parastomal Hernia Using a Porcine Dermal Collagen (Permacol™) Implant," *Dis. Colon Rectum* (2007), p. 1465, 50.

International Search Report and Written Opinion for PCT/US2011/025224 dated Aug. 29, 2011, from the International Searching Authority of the European Patent Office.

Israelsson, "Preventing and Treating Parastomal Hernia," *World J. Surg.* (2005), p. 1086-1089, 29.

Jänes et al., "Randomized Clinical Trial of the Use of a Prosthetic Mesh to Prevent Parastomal Hernia," *British Journal of Surgery* (2004), p. 280-282, 91.

Kasperk et al., "The Repair of Large Parastomal Hernias Using a Midline Approach and a Prosthetic Mesh in the Sublay Position," *The American Journal of Surgery* (2000), p. 186-188, 179.

Kish et al., "Acellular Dermal Matrix (AlloDerm): New Material in the Repair of Stoma Site Hernias," *The American Surgeon* (2005), p. 1047-1050, 71.

Lochan et al., "Letter 1: Parastomal Hernia," *Br. J. Surg.*(2003), p. 784-793, 90, abstract.

Petersen et al., "Ventral Rectus Fascia Closure on Top of Mesh Hernia Repair in the Sublay Technique," *Plastic and Reconstructive Surgery* (2004), p. 1754-1760, 114(7).

* cited by examiner

ABDOMINAL WALL TREATMENT DEVICES

This application claims priority under 35 U.S.C. § 119 to U.S. Provisional Application No. 61/306,006, which was filed on Feb. 19, 2010.

The present disclosure relates to devices and methods for treating or repairing openings in body cavities, including abdominal openings.

There are various situations in which it may be very difficult or impossible for surgeons to close abdominal incisions. For example, after trauma or with certain diseases, the abdominal viscera may swell, making it very difficult to return the abdominal contents to the abdomen after creating a relatively large incision. In addition, for very large (e.g., obese) patients, or for patients who have lost a portion of their abdominal wall due, for example, to prior surgical resection or trauma, it can be difficult or impossible to close the abdominal wall completely. However, various devices and methods for closing abdominal incisions have had certain disadvantages.

In addition, for certain surgeries, it may be necessary to access the abdominal cavity multiple times. However, it is generally undesirable to make multiple incisions at the same location while a primary incision is still healing. Further, closing an incision that has been accessed multiple times can lead to increased risk of infection, and often, such incisions are closed by secondary approximation, which can be unpleasant for the patient.

Accordingly, there is a need for improved devices for closing abdominal incisions or incisions or defects in fascia.

An abdominal or fascia treatment device is provided. The device may comprise a first synthetic polymeric material and an acellular tissue matrix attached to a peripheral border of the synthetic polymeric material such that the acellular tissue matrix can be secured to tissues surrounding an opening in a body cavity to close the body cavity without attaching the first synthetic polymeric material to tissue.

A method of treating an abdominal or fascia opening is provided. The method may comprise positioning a synthetic polymeric material in the opening, wherein the synthetic polymeric material is attached to an acellular tissue matrix along a peripheral border of the synthetic polymeric material. The method further comprises securing the acellular tissue matrix to tissues surrounding a peripheral border of the abdominal opening to close the opening.

An abdominal or fascia treatment device is provided. The device may comprise a sheet of acellular tissue matrix, wherein the sheet includes an elongated opening, and on opposite sides of the opening, multiple reinforced holes for receiving sutures.

DESCRIPTION OF EXEMPLARY EMBODIMENTS

In this application, the use of the singular includes the plural unless specifically stated otherwise. In this application, the use of "or" means "and/or" unless stated otherwise. Furthermore, the use of the term "including", as well as other forms, such as "includes" and "included", is not limiting.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "acellular tissue matrix," as used herein, refers generally to any tissue matrix that is substantially free of cells and other antigenic material. Skin, parts of skin (e.g., dermis), and other tissues such as blood vessels, heart valves, fascia and nerve connective tissue may be used to create acellular matrices within the scope of the present disclosure.

The term "abdominal defect," as used herein refers generally to a disruption in the abdominal wall. The disruption can include a hole that passes through the entire abdominal wall, such as an incision through the wall, or can include an incision or defect in one or more layers of the abdominal wall, such as the skin and subcutaneous fat.

Figure 1:
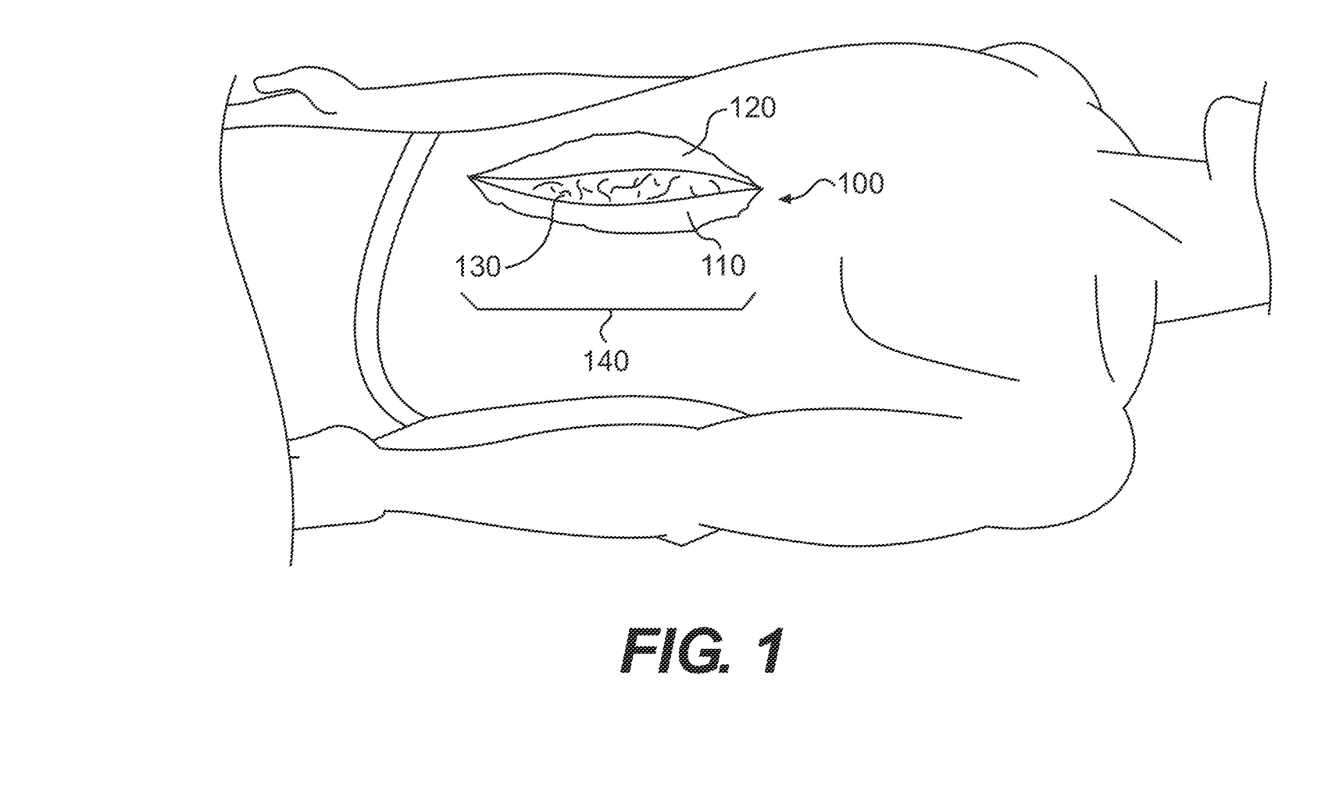
FIG. 1 illustrates a device and method for treating abdominal openings, according to certain embodiments.

FIG. 1 illustrates a device and method for treating abdominal openings, according to certain embodiments. According to certain embodiments, the device 100 can be used to close an abdominal defect 140, including, for example, an incision created by surgery. As shown in FIG. 1, the device 100 can assist in closure of a midline incision, or can be used to assist in closure of other incisions (e.g., more laterally positioned incisions, transverse incisions, or oblique incisions).

As described further below, the device 100 can include one or more sheets of material 110, 120 that can be used to connect opposing edges of a wound, surgical incision, or other abdominal defect 140. For example, when the existing fascia or other tissue surrounding the defect 140 is insufficient, for whatever reason, the device 100 can provide additional material to allow tissues (e.g., fascia) surrounding a defect 140 to be connected and to cover the entire defect 140. In certain embodiments, the device 100 can be used to cover the defect 140 temporarily until a final closure is desired or possible. For example, if final closure is not possible due to swelling of abdominal contents, the device 100 can be used to close the abdomen until swelling abates. In addition, the device 100, can provide an access site to allow multiple surgeries. In addition, the device 100 can be adjusted during two or more surgeries to allow more normal surgical closure, as described further below.

In certain embodiments, the sheets 110, 120 of the device 100 include a biologic material, including an acellular tissue matrix, such as a dermal acellular tissue matrix. In addition, in certain embodiments, the sheets 110, 120 further include a synthetic polymeric material that is attached to the acellular tissue matrix. Various embodiments of the device 100, are described with reference to FIGS. 2-5D below (labeled 200, 300).

Figure 2:
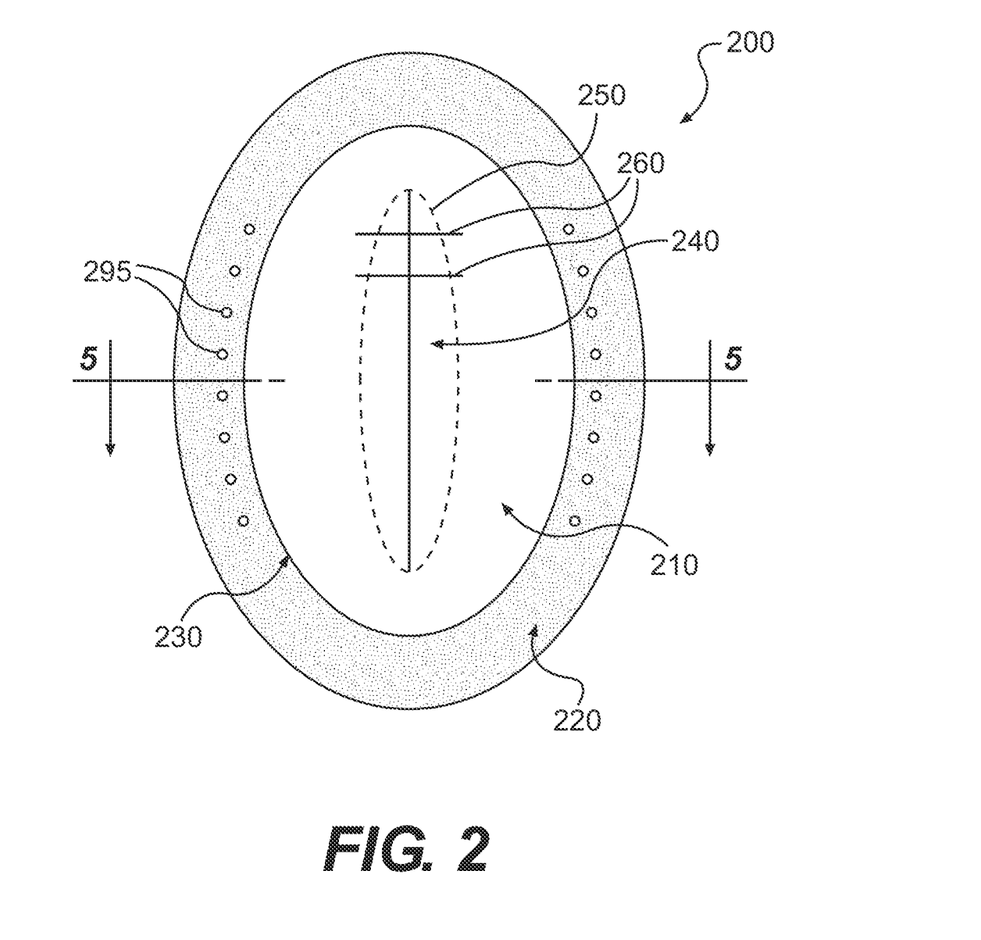
FIG. 2 illustrates a device for treating abdominal openings, according to certain embodiments.

FIG. 2 illustrates a device 200 for treating abdominal defects, according to certain embodiments. In certain embodiments, the device 200 includes a first synthetic polymeric material 210 and an acellular tissue matrix 220 attached to an entire peripheral border 230 of the synthetic polymeric material 210. In use, the acellular tissue matrix 220 can be secured to tissues surrounding a defect 140 in a body cavity to close the body cavity (e.g., the abdomen) without attaching the first synthetic polymeric material to tissue. For example, when an abdominal incision is formed (either midline or at another location), it may be difficult to close the incision completely. This may be due to swelling of abdominal contents, large patient size, and/or loss of tissue due to prior surgery, trauma or disease. In addition, in some cases, it may be desirable to access the surgical site again, e.g., to perform additional surgeries. The device 200 can assist in closure of an incision or other defect and can be used to re-access the surgical site and/or to close the defect after problems that prevented normal closure abate (e.g., swelling diminishes or subsequent surgical steps are complete).

As used herein, the term "synthetic polymeric material" includes any polymeric material sheet produced by man, either from a chemical reaction, or by assembling a natural material to produce a sheet. For example, polymers produced by man can include, polyethylenes or polyamides. Materials produced by assembling a natural material can include, for example, sheets produced from silk.

Figure 3:
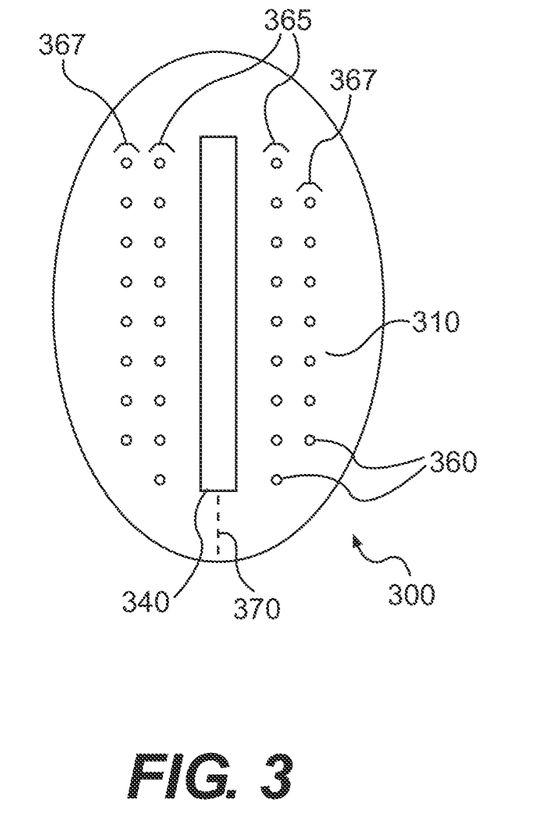
FIG. 3 illustrates a device for treating abdominal openings, according to certain embodiments.

During initial implantation, the synthetic polymeric material 210 with an acellular tissue matrix 220 attached to its peripheral border 230 to form a joint 235 (see FIGS. 5A-5D) is positioned in the defect in the abdominal wall. Next, the acellular tissue matrix is attached to tissues surrounding a peripheral border of the abdominal defect to close the defect. Generally, for a midline incision, the acellular tissue matrix 220 will be secured to abdominal fascia (e.g., the rectus sheath), thereby acting as an extension of the rectus sheath, which is normally used to close midline abdominal incisions. The acellular tissue matrix can be attached to the tissues using typical sutures, surgical staples, or clips, or other suitable connecting mechanisms, as are known in the art. In certain embodiments, the acellular tissue matrix 220 can be connected by passing sutures through the acellular tissue matrix 220. In certain embodiments, the sutures can be passed through preformed openings 295, which may be reinforced (or openings 360, as shown in FIG. 3).

Various materials can be used to produce the synthetic polymeric material 210 and acellular tissue matrix 220 (collectively "materials"). Generally, both materials should be sterile or aseptic and should possess suitable biomechanical properties to prevent rupture or tearing during use. In addition, in some embodiments, the mechanical properties of the materials are compatible to provide even stress distributions relative to the different materials to prevent failure, as described in more detail below. In addition, the synthetic material should be generally inert or biologically compatible to prevent undue inflammation. Suitable synthetic materials can include, for example, GORE-TEX® (or other polytetrafluroethylene materials), MARLEX® (high density polyethylene), or prolene. In certain embodiments, the synthetic materials can include synthetic, resorbable materials over part or all of their dimensions. In addition, the materials may be coated with therapeutic agents, (e.g., anti-adhesive coatings, antimicrobials, etc.).

The acellular tissue matrix can be selected to provide a variety of different biological and mechanical properties. For example, the acellular tissue matrix can be selected to allow tissue ingrowth and remodeling to allow regeneration of tissue normally found at the site where the matrix is implanted. For example, the acellular tissue matrix, when implanted on or into fascia, may be selected to allow regeneration of the fascia without excessive fibrosis or scar formation. In addition, the acellular tissue matrix should not elicit an excessive inflammatory reaction and should ultimately be remodeled to produce tissue similar to the original host tissue. In certain embodiments, the acellular tissue matrix can include ALLODERM® or Strattice™, which are human and porcine acellular dermal matrices respectively. Alternatively, other suitable acellular tissue matrices can be used, as described further below.

Generally, both the synthetic polymeric material 210 and acellular tissue matrix 220 should possess mechanical properties such that the materials will not fail (i.e., rupture or tear) during use. In addition, the materials should have sufficient flexibility and elasticity to be handled by a surgeon when implanted, to be shaped to allow coverage of underlying structures, and to allow stretching during patient movement to provide even stress distribution to adjacent tissues without tearing. It will be understood that these properties can be varied by altering the general material properties (e.g., tensile strength and elastic properties), as well as the structural characteristics of the materials (e.g., thickness). In certain embodiments, the materials will have been selected such that the materials can withstand a tensile force of at least 20N without failure. In some embodiments, the materials can withstand a minimum force per unit width, such as at least 20N/cm, at least 24N/cm, or higher, depending on the patient. In addition, in certain embodiments, the materials are selected to allow retention of sutures. In some embodiments, the materials have a suture retention strength of at least 20N.

In certain embodiments, the materials 210, 220 may be selected and sized such that, during use, the stress distribution across the materials remains relatively even. For example, in various embodiments, the synthetic polymeric material 210 and the acellular tissue matrix 220 can be selected such that the ultimate tensile strength and/or elastic properties over typical operating ranges are relatively equal, or within a certain range of one another. In addition, the mechanical properties of the joint 235 between the synthetic polymeric material 210 and acellular tissue matrix 220 can be similarly matched with those of the synthetic polymeric material 210 and/or acellular tissue matrix 220. For example, in certain embodiments, the ultimate strength of the synthetic polymeric material 210 differs from the ultimate strength of the acellular tissue matrix 220 by less than 20%, less than 15%, less than 10%, less than 5%, or any value between those percentages. In certain embodiments, the elastic modulus of the synthetic polymeric material 210 differs from the elastic modulus of the acellular tissue matrix 220 by less than 20%, less than 15%, less than 10%, less than 5%, or any value between those percentages.

Figure 5A:
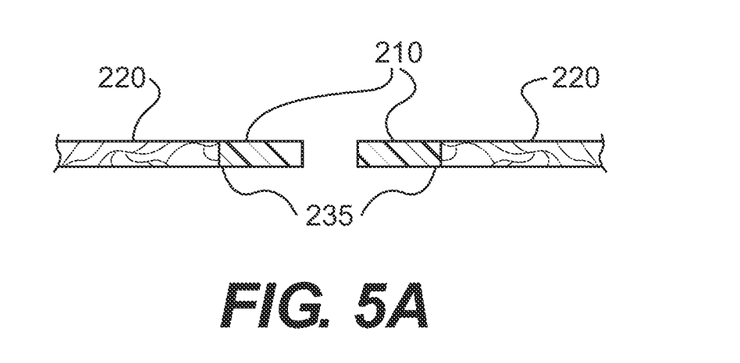
FIGS. 5A-5D are cross sectional views of the device of FIG. 2, according to various exemplary embodiments.
Figure 5B:
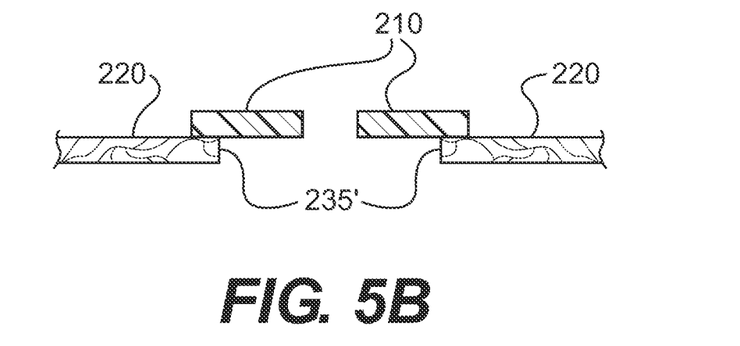
Figure 5C:
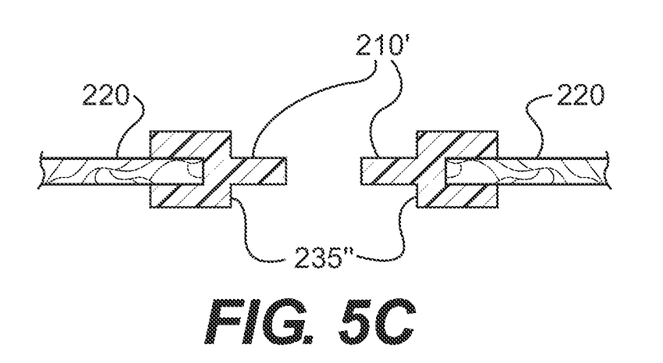
Figure 5D:
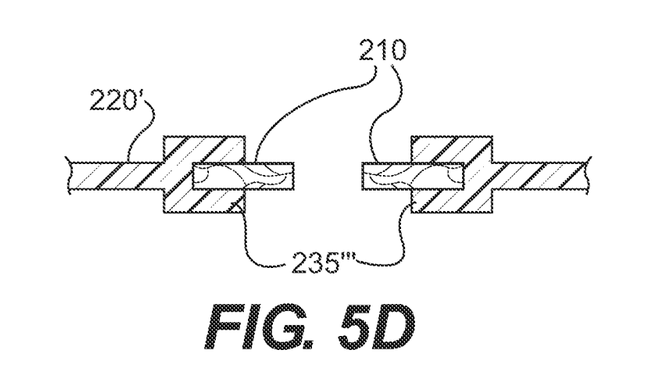

The synthetic polymeric material 210 and acellular tissue matrix 220 can be attached to one another using a number of devices or techniques. For example, the materials 210, 220 may be connected using various sutures, staples, tacks, or adhesives including permanent sutures, such as prolene sutures. The materials 210, 220 can be connected to one another in a number of configurations. FIGS. 5A-5D are cross sectional views of the device of FIG. 2, according to various exemplary embodiments. As illustrated, the materials can be attached at an end-to-end joint 235 (FIG. 5A), by an overlapping joint 235' (FIG. 5B), with the synthetic material 210 forming a bifurcated pocket joint 235" (FIG. 5C), or with the acellular tissue matrix forming a bifurcated pocket joint 235'" (FIG. 5D).

Figure 6:
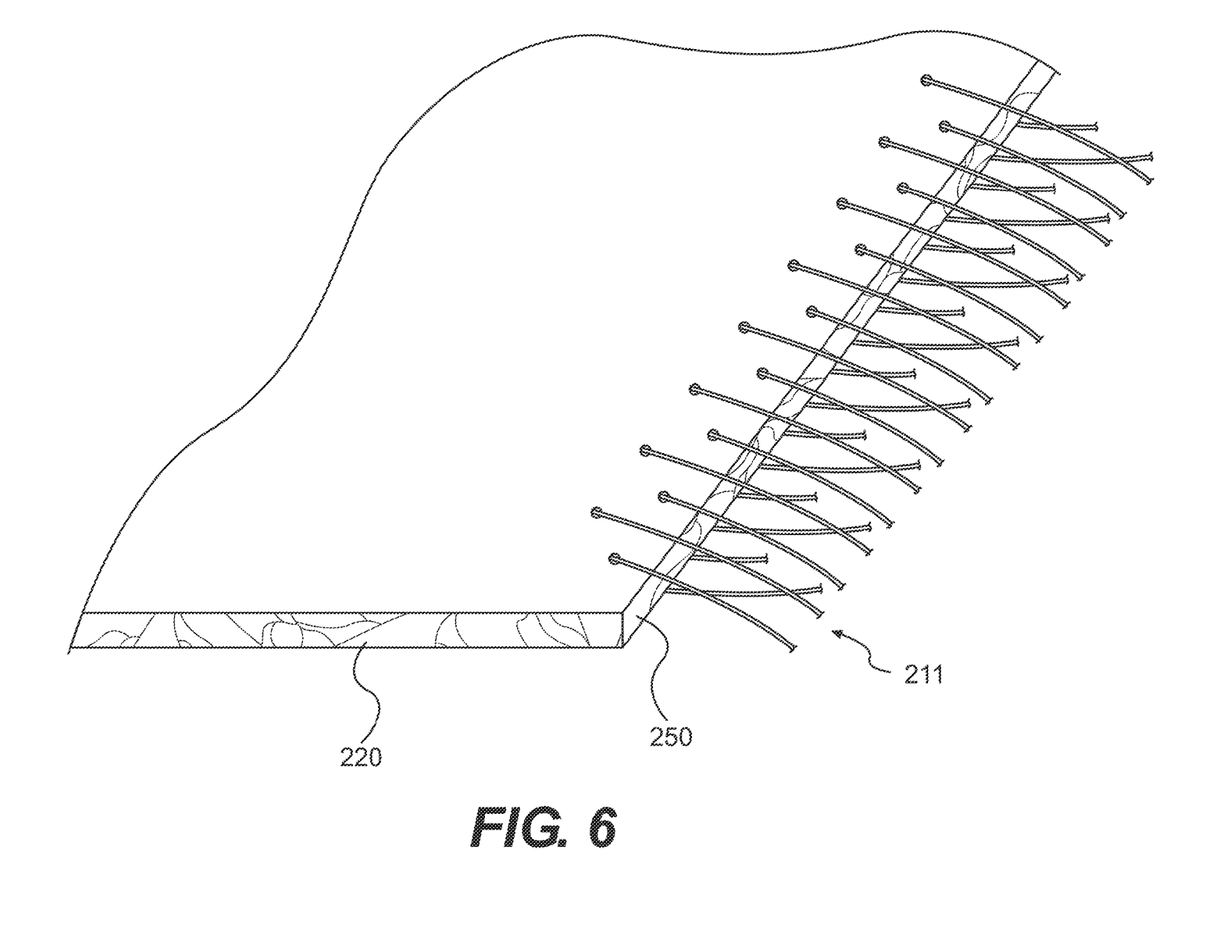
FIG. 6 illustrates a perspective view of the device of FIG. 2, according to certain embodiments.

In certain embodiments, the materials can be attached by weaving one or both of the materials to the other. For example, FIG. 6 illustrates an acellular tissue matrix 220 that is attach to a woven synthetic material 211 at a joint 250. In other embodiments, the biologic material 220 can be woven, or both materials 220, 211 are woven to produce a joint 250 with sufficient mechanical properties to prevent failure during use, while allowing relatively even stress distribution.

As described above, the acellular tissue matrix 220 can be secured to tissues surrounding a defect 140 in a body cavity to close the defect without attaching the first synthetic polymeric material to tissue. In this way, the acellular tissue matrix 220, which is selected to allow tissue ingrowth and remodeling, is the only material (other than sutures or other connecting devices) that is connected, attached, and/or anchored to the tissue. Further, after attachment, the fascia or other tissue can begin ingrowth and remodeling.

In addition, as noted above, in some embodiments, it may be desirable to access a surgical site/incision multiple times, and/or to ultimately close the incision permanently after completion of subsequent treatments or after changes in a patient's condition (e.g., diminished swelling of abdominal contents). Accordingly, in some embodiments, the synthetic polymeric material can include an opening 240 or can be cut, without cutting adjacent tissue, to allow repeated access. The opening 240 can then be resealed with sutures 260 or other devices. In some embodiments, part of the synthetic polymeric material (delimited by oval 250) can be removed, and the synthetic polymeric material 210 can be shortened to provide additional tension on the incision margins or to remove excess or contaminated materials.

In some cases, it may be desirable to completely remove the synthetic polymeric material 210 while leaving the acellular tissue matrix 220 attached to tissues. For example, the synthetic polymeric material 210 may be removed at a later time, e.g., after swelling has diminished or subsequent surgeries have been completed, and the acellular tissue matrix 220 can be left attached to the tissues surrounding the peripheral border of the abdominal defect. In addition, the abdominal defect can then be closed after removing the synthetic polymeric material 210 by attaching remaining portions of the acellular tissue matrix 220 to one another using sutures, staples, or other surgical means. In various embodiments, the acellular tissue matrix 220 will bolster the fascia or other tissue around the defect to prevent reopening or dehiscence. In addition, the acellular tissue matrix can provide additional tissue in cases where there is insufficient tissue present for normal fascia closure.

In some embodiments, as described above, the acellular tissue matrix 220 can include openings 295, and the openings can be used to receive sutures for closing the abdominal opening. In some embodiments, the openings 295 can be reinforced, as described further below.

In certain embodiments devices for treating abdominal defects which do not include a synthetic polymeric material in a sheet are provided, as described above. Such devices may include only an acellular tissue matrix, but may be useful for closing certain incisions in the presence of the above noted challenges (e.g., swelling, insufficient tissue, need to access surgical sites multiple times). FIG. 3 illustrates a device 300 for treating abdominal defects, according to certain embodiments. The device 300 comprises a sheet 310 of acellular tissue matrix, wherein the sheet 310 includes an elongated opening 340, and on opposite sides of the opening 340 multiple holes 360 for receiving sutures, and wherein the multiple holes 360 are reinforced. The device 300 can be secured to wound margins (e.g., via fascia using sutures), and the reinforced holes 360 can receive sutures that provide tension to the device 300 and wound margins to close the wound or incision.

Figure 4:
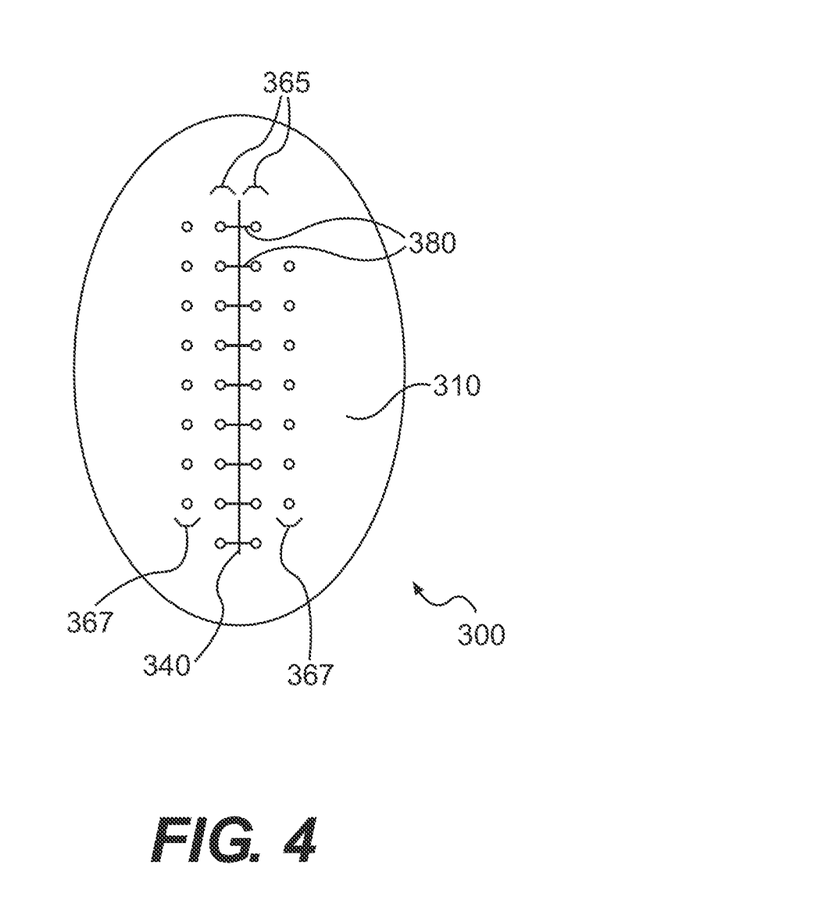
FIG. 4 illustrates the device of FIG. 3, as it may be used for treating abdominal openings, according to certain embodiments.

In some cases, the opening 340 can be reopened, for example, to perform a subsequent operation, clean a wound/abdominal site, or for any other purpose. In addition, in some cases, the device 300 can have multiple sets of reinforced holes 360, to allow the device to be sutured with at varying distances, for example, to provide increasing tension to wound margins, or to remove excess material. For example, in some embodiments, the preformed holes 360 include two or more rows 365, 367 of holes positioned on each side of the elongated opening 340, and sutures can be placed through holes at selected distances apart. For example, as shown in FIG. 4, sutures may initially be attached through a first row of holes 365 nearest the opening 340, to close an incision. However, later, as swelling of abdominal viscera decreases, or as tissues stretch, a surgeon may add additional sutures or replace the sutures, passing the sutures through openings 367. In this way, the wound or incision margins can be pulled closer together as the sutures are tightened or shortened.

As shown in FIGS. 3 and 4, the device 300 can include a single sheet of material. However, in some embodiments, two or more pieces of acellular tissue matrix 310 may be used. For example, the device of FIG. 3 can be divided into two pieces along a line extending from line 370 to produce two pieces of material. The two pieces can be implanted on opposite sides of a wound or incision and sutured in place to close the wound or incision, as described above.

The openings 360 (and 295) can be reinforced in a number of ways. In some embodiments, the openings 360 can be reinforced using a biocompatible adhesive placed around the rim or edge of the openings 360. Suitable adhesives include, for example, fibrin glue, cyanoacrylate-based tissue adhesives (e.g., DERMABOND®), and chitosan tissue adhesives. In some embodiments, the rim or edges of the openings 360 can be crosslinked to increase their strength and prevent tearing (e.g., using chemical or radiation induced cross-linking).

Suitable Acellular Tissue Matrices

As noted above, the term "acellular tissue matrix," as used herein, refers generally to any tissue matrix that is substantially free of cells and other antigenic material. Skin, parts of skin (e.g., dermis), and other tissues such as blood vessels, heart valves, fascia and nerve connective tissue may be used to create acellular matrices within the scope of the present disclosure.

In general, the steps involved in the production of an acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and/or one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents (e.g., TRITON X-100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 1% TRITON X-100™ in RPMI media with Gentamicin and 25 mM EDTA (ethylenediaminetetraacetic acid). In some embodiments, the tissue is incubated in the decellularization solution overnight at 37° C. with gentle shaking at 90 rpm. In certain embodiments, additional detergents may be used to remove fat from the tissue sample. For example, in some embodiments, 2% sodium deoxycholate is added to the decellularization solution.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM CaCl2 and 20 mM MgCl2). Optionally, an antibiotic solution (e.g., Gentamicin) may be added to the DNase solution. Any suitable buffer can be used as long as the buffer provides suitable DNase activity.

While an acellular tissue matrix may be made from one or more individuals of the same species as the recipient of the acellular tissue matrix graft, this is not necessarily the case. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Elimination of the α-gal epitopes from the collagen-containing material may diminish the immune response against the collagen-containing material. The α-gal epitope is expressed in non-primate mammals and in New World monkeys (monkeys of South America) as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation of collagen-containing material from these mammals into primates often results in rejection because of primate anti-Gal binding to these epitopes on the collagen-containing material. The binding results in the destruction of the collagen-containing material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, in some embodiments, when animals that produce α-gal epitopes are used as the tissue source, the substantial elimination of α-gal epitopes from cells and from extracellular components of the collagen-containing material, and the prevention of re-expression of cellular α-gal epitopes can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the tissue sample is treated with α-galactosidase at a concentration of 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used as long as sufficient removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals see co-pending U.S. application Ser. No. 10/896,594 and U.S. Pat. No. 6,166,288, the disclosures of which are incorporated herein by reference in their entirety. In addition, certain exemplary methods of processing tissues to produce acellular matrices with or without reduced amounts of or lacking alpha-1,3-galactose moieties, are described in Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is incorporated by reference in its entirety.

After the acellular tissue matrix is formed, histocompatible, viable cells may optionally be seeded in the acellular tissue matrix to produce a graft that may be further remodeled by the host. In some embodiments, histocompatible viable cells may be added to the matrices by standard in vitro cell co-culturing techniques prior to transplantation, or by in vivo repopulation following transplantation. In vivo repopulation can be by the recipient's own cells migrating into the acellular tissue matrix or by infusing or injecting cells obtained from the recipient or histocompatible cells from another donor into the acellular tissue matrix in situ. Various cell types can be used, including embryonic stem cells, adult stem cells (e.g. mesenchymal stem cells), and/or neuronal cells. In various embodiments, the cells can be directly applied to the inner portion of the acellular tissue matrix just before or after implantation. In certain embodiments, the cells can be placed within the acellular tissue matrix to be implanted, and cultured prior to implantation.

The invention claimed is:
1. An abdominal or fascia treatment device, comprising:
a sheet of synthetic polymeric material; and an acellular tissue matrix attached to and extending from a peripheral border of the sheet of synthetic polymeric material such that the acellular tissue matrix can be secured to tissues surrounding a defect in a wall of a body cavity to close the body cavity without attaching the sheet of synthetic polymeric material to tissue, wherein the acellular tissue matrix defines a peripheral portion of the abdominal or fascia treatment device, and the sheet of synthetic polymeric material defines a central portion of the abdominal or fascia treatment device, and wherein the sheet of synthetic polymeric material includes an elongated opening extending across a portion of the sheet of synthetic polymeric material, the elongated opening being configured to provide access to the body cavity in an open configuration and close the body cavity in a closed configuration.

2. The device of claim 1, wherein an ultimate strength of the sheet of synthetic polymeric material differs from an ultimate strength of the acellular tissue matrix by less than 20%.

3. The device of claim 1, wherein an elastic modulus of the sheet of synthetic polymeric material differs from an elastic modulus of the acellular tissue matrix by less than 20%.

4. The device of claim 1, wherein the acellular tissue matrix is a dermal acellular tissue matrix.

5. The device of claim 4, wherein the dermal tissue matrix is a human tissue matrix.

6. The device of claim 4, wherein the dermal tissue matrix is a porcine tissue matrix.

7. The device of claim 1, wherein the acellular tissue matrix includes preformed holes disposed on each side of the sheet of synthetic polymeric material.

8. An abdominal or fascia treatment device, comprising:
    a sheet of synthetic polymeric material, the sheet of synthetic polymeric material being without perforations at a central portion of the sheet of synthetic polymeric material except for an elongated opening extending across a portion of the sheet of synthetic polymeric material; and
    an acellular tissue matrix attached to and extending from a peripheral border of the sheet of synthetic polymeric material such that the acellular tissue matrix can be secured to tissues surrounding a defect in a wall of a body cavity to close the body cavity without attaching the sheet of synthetic polymeric material to tissue,
    wherein the acellular tissue matrix defines a peripheral portion of the abdominal or fascia treatment device, and the sheet of synthetic polymeric material defines a central portion of the abdominal or fascia treatment device, and
    wherein the elongated opening is configured to provide access to the body cavity in an open configuration and close the body cavity in a closed configuration.

9. The device of claim 7, wherein the preformed holes are reinforced.

10. The device of claim 9, wherein the reinforced holes include an adhesive.

11. The device of claim 10, wherein the adhesive includes a cyanoacrylate adhesive.

12. The device of claim 10, wherein the adhesive includes fibrin.

13. A method of treating an abdominal or fascia defect, comprising:
    positioning a sheet of synthetic polymeric material of an abdominal or fascia treatment device in or on a defect in a body cavity, wherein an acellular tissue matrix is attached to and extends from a peripheral border of the sheet of synthetic polymeric material such that the acellular tissue matrix can be secured to tissues surrounding the defect in a wall of the body cavity to close the body cavity without attaching the sheet of synthetic polymeric material to tissue, wherein the acellular tissue matrix defines a peripheral portion of the abdominal or fascia treatment device, and the sheet of synthetic polymeric material defines a central portion of the abdominal or fascia treatment device, and wherein the sheet of synthetic polymeric material includes an elongated opening extending across a portion of the sheet of synthetic polymeric material, the elongated opening being configured to provide access to the body cavity in an open configuration and close the body cavity in a closed configuration; and
    securing the acellular tissue matrix to tissue surrounding a peripheral border of the defect to close the defect.

14. The method of claim 13, further including removing the sheet of synthetic polymeric material at a later time while leaving the acellular tissue matrix attached to the tissues surrounding the peripheral border of the abdominal defect.

15. The method of claim 14, further including closing the defect in the body cavity after removing the sheet of synthetic polymeric material by attaching remaining portions of the acellular tissue matrix to one another.

16. The method of claim 15, wherein attaching the remaining portions of the acellular tissue matrix to one another includes passing sutures through preformed holes in the acellular tissue matrix.

17. The method of claim 16, wherein the preformed holes are reinforced.

18. The method of claim 17, wherein the reinforced holes include an adhesive.

19. The method of claim 18, wherein the adhesive includes a cyanoacrylate adhesive.

20. The method of claim 18, wherein the adhesive includes fibrin.

* * * * *